United States Patent [19]

Reale

[11] 4,135,517

[45] Jan. 23, 1979

[54] FEMORAL PROSTHESIS TRIAL FITTING DEVICE

[75] Inventor: Richard C. Reale, Park Ridge, N.J.

[73] Assignee: Minnesota Mining and Manufacturing Company, St. Paul, Minn.

[21] Appl. No.: 817,551

[22] Filed: Jul. 21, 1977

[51] Int. Cl.² .................... A61B 17/00; A61F 1/24
[52] U.S. Cl. ........................... 128/303 R; 3/1.913; 128/92 CA; 128/92 E; 128/2 S
[58] Field of Search .................... 3/1.9, 1.91, 1.912, 3/1.913, 1; 128/92 C, 92 CA, 92 E, 303 R, 2 S

[56] References Cited

U.S. PATENT DOCUMENTS

| 3,813,699 | 6/1974 | Giliberty | 3/1.913 |
| 3,818,512 | 6/1974 | Shersher | 3/1.912 |
| 3,863,273 | 2/1975 | Averill | 3/1.91 |
| 4,044,403 | 8/1977 | D'Errico | 3/1.913 |

OTHER PUBLICATIONS

The Bechtol Total Hip System, Orthopedic Catalog, Richards Mfg. Co., Inc., Memphis, Tenn., pp. 1-5.

*Primary Examiner*—Ronald L. Frinks
*Attorney, Agent, or Firm*—Cruzan Alexander; Donald M. Sell; Edward T. Okubo

[57] ABSTRACT

A trial fitting device for an implantable femoral prosthesis comprising a trial head, a bearing insert removably fitting within the trial head and a femoral prosthesis stem or a trial handle onto which said bearing insert is removably rotatably mounted is disclosed. Differently sized trial heads can be quickly substituted utilizing the trial fitting device of the present invention.

7 Claims, 3 Drawing Figures

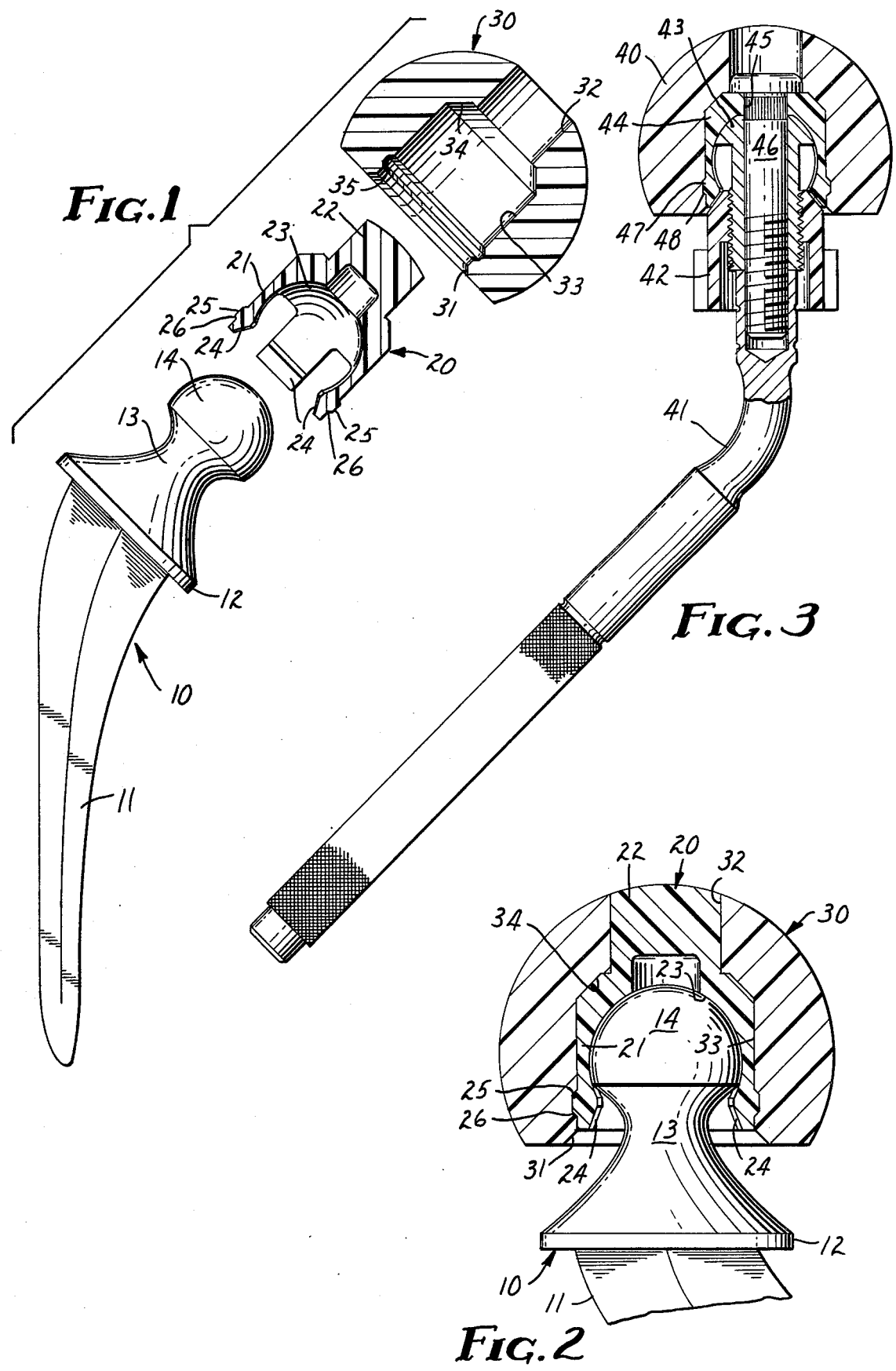

FEMORAL PROSTHESIS TRIAL FITTING DEVICE

BACKGROUND OF THE INVENTION

The present invention relates to prosthetic ball and joint sockets for the human hip and particularly to a trial head and insert for an implantable hip joint prosthesis. The head and insert are unique in that they are self-locking to the the ball end of an intramedullary stem and yet can be instantly and easily released therefrom without the need for any tools.

Prosthetic ball and socket joints for surgical human hip repair have been known since about 1948. During the early years of this surgical joint repair, only the ball was replaced, the artificial ball being seated in the natural acetabular socket of the hip. Experience showed that friction of the artificial ball against the natural acetabular socket was unsatisfactory, causing wear of the acetabulum bearing surface and resulting in excessive progressive pain and stiffening of the hip joint.

The next phase of development resulted in the surgical procedure known as total hip replacement wherein not only the femoral head was replaced by a prosthesis but also the acetabular socket was enlarged and an acetabular prosthetic socket implanted. The natural femoral head is replaced by a metal intramedullary stem which terminates in a collar portion and neck portion with an offset ball or head portion which has a highly polished spherical bearing surface. The prosthetic acetabular socket component is usually in the form of a concave, cup-shaped, socket member shaped to receive the ball-shaped head of the femoral component. The bearing surface of the acetabular socket component is usually made of a synthetic resin such as an ultra-high molecular weight polyethylene. The combination of a highly polished metal surface bearing against a smooth durable synthetic resin provides for low-friction long-lasting joint operation.

While these total hip replacement prostheses have been quite successful, the surgical procedure involved is very complicated and time consuming. Because of the length of time required for the operation, the risk of infection and complication is very high and the surgical trauma is excessive, particularly for elderly patients. For these reasons, there have been recent developments which suggest that partial hip replacements are preferred for an increasing percentage of hip procedures. Averill, U.S. Pat. No. 3,863,273, describes one of these improved partial prosthetic hip implant joints having a femoral intramedullary stem unit with a reduced size spherical metal ball which can freely rotate within a plastic bearing insert which is locked within a metal head which seats within the natural acetabular socket. This device is recommended for use when fractures of the femoral neck or other conditions of the femur occur but in which the function of the acetabulum is unaffected. Not only is this partial hip joint replacement a faster, easier and less traumatic surgical procedure but it also results in a quicker return to full mobility for the patient. This modern partial hip replacement prosthesis works much better than the earlier prosthetic joints because most of the hip movement occurs by rotation of the metal femoral ball within the spherical socket of the bearing insert. If excessive joint motion is required, beyond the capability of the femoral ball/bearing insert, then the outer metal head rotates slightly within the natural acetabular socket, to accommodate the excessive joint motion.

Since the partial hip implant utilizes the natural acetabular socket, many sizes of prosthetic heads must be available to simulate the natural femoral head and insure a close fit between the natural acetabular socket and the prosthetic head. Prosthetic heads for partial hip implants are commonly available with spherical radii of 20.6 mm, 21.4 mm, 22.2 mm, 23.0 mm, 23.8 mm, 24.6 mm, 25.4 mm, 26.2 mm and 26.9 mm.

SUMMARY OF THE INVENTION

The present invention relates to a trial head and bearing insert particularly adapted for an implantable partial hip joint prosthesis. While the outer head which will be used for the final implant is normally made of metal, the trial heads are made of plastic to reduce possibility of damaging the acetabulum while the trial heads are inserted for trial fit. Further, the surface of the final metal outer heads is highly polished and the use of these expensive prosthetic devices for trial purposes would expose them to the possibility of unnecessary damage.

Trial fitting of the prosthetic head into the natural acetabulum to determine the proper size is a time consuming process which tends to prolong the surgical procedure. A too large head tends to stick or lodge in the acetabular cavity and pull loose from the femoral prosthesis and must then be removed with a special removal tool.

The devices of the present invention comprise a system whereby a trial bearing insert can be quickly snapped onto the ball of a trial femoral prosthesis or onto a handle having a similarly shaped and sized ball. The insert can then be quickly snapped into a trial head and the combination tested for fit within the natural acetabular socket. The combination can then be removed from the acetabular socket by pulling on the handle or by pulling on the femoral stem with no risk of the trial head becoming detached from the assembly and sticking in the acetabulum. Slight gloved finger pressure on the bearing insert projecting at the rear of the trial head will instantly and easily release the femoral ball/bearing insert from the trial head after which an appropriately differently sized trial head can be snapped into place and the process repeated. When the appropriate size trial head has thus been selected, it can be removed, the trial bearing insert also snapped off, and the final prosthesis assembly put together and inserted in place in the normal manner.

BRIEF DESCRIPTION OF THE DRAWINGS

In the accompanying diagrammatic drawings which illustrate the invention:

FIG. 1 is an exploded view, partially in section, showing a representative femoral stem prosthesis, the bearing insert and trial head of the present invention;

FIG. 2 is an enlarged partial view, in section, of the components of FIG. 1 assembled for trial insertion; and FIG. 3 is a view, partly in section, of another embodiment of the invention utilizing a trial handle in place of the femoral stem prosthesis.

DETAILED DESCRIPTION OF THE INVENTION

Referring more particularly to the drawings, FIG. 1 shows a representative femoral stem prosthesis 10 intended for partial hip replacement. The stem 11 and collar 12, as illustrated are of the "Aufranc-Turner" type although the stem and/or collar could be of various designs such as the "Moore" type or "Charnley"

type or could alternatively be of other stem and/or collar designs. The stem 11 is intended to be surgically implanted in the medullary cavity of a human femur and the collar 12 provides a certain amount of weight bearing surface against the resectioned end of the natural femur. Neck portion 13 reduces in taper as described in Averill, U.S. Pat. No. 3,863,273, to provide accommodation for rotation of the femoral prosthesis within the bearing insert. The femoral ball 14 is a highly polished metal spherical surface of reduced radius compared with the natural femoral ball. The spherical surface of ball 14 must, however, be greater than hemispherical, for a purpose to be hereinafter described. The femoral stem 11 is usually formed of metal such as a cobalt chrome alloy or stainless steel. Alternatively, for trial usage, a handle of suitable configuration but having a similarly sized and shaped neck 13 and ball 14 could be used in the present invention, or as will be described later, a completely different style of trial handle can be used.

Bearing insert 20 of the present invention comprises a substantially cylindrical body having a plurality of depending separated flexible arms 21 which have a length greater than the height of the spherical surface of femoral ball 14, and a more or less rigid cylindrical rearward protrusion 22. As shown in the drawings, the cylindrical rearward protrusion 22 of bearing insert 20 is of reduced diameter from that of the main body, the two cylindrical portions being connected by tapered ramp portion. The bearing insert 20 is preferably made of a low-friction material having sufficient strength and flexibility for the purpose. Preferred materials are acetal resins exemplified by "Celcon" or "Delrin" although other materials such as polyethylene or polypropylene might also be used. It is unnecessary to use materials such as silicone which are physiologically inert since the device is used for trial fitting purposes only and not for permanent implant although, of course, such materials could be used if economically justified. It is preferred to use materials which can stand repeated sterilization cycles so that they can be reused. It is also contemplated that the bearing insert could be formed of a combination of several materials including some, or all, metal.

The inner cavity 23 of bearing insert 20 is spherical in shape and slightly larger than the size of the femoral ball 14, the slight tolerance contributing to easy operation of the device. The inner spherical cavity surface 23 should comprise a larger segment of a sphere than does the femoral ball 14 so that the inner curvature of the flexible arms 21 extends past the spherical surface of the femoral ball 14 to assist operation of the device as will be explained hereafter. The ends of the arms 21 have a concave chamfer 24, as shown, to facilitate entry of the femoral ball 14 into the cavity 23. The outer cylindrical surfaces of the arms 21 have an external annular ring segment 25 adjacent the free end thereof and the inner surfaces thereof are formed with a tapered leading edge 26, preferably a 45° taper. The annular ring segment 25 provides locking action when seated into a corresponding annular groove 35 in the outer trial head 30. The trailing edge of the annular ring segment 25 may be tapered as shown or may be at 90° to the cylindrical surface of the arms 21. The annular ring segment 25 may have an outer flat cylindrical surface as shown or may be alternatively V-shaped or have a semi-circular cross-section with, of course, a complementarily shaped groove 35 in the trial head 30. The flat configuration shown is preferable because of resistance to damage. The remainder of the external shape of the bearing insert 20 may be altered for appearance, construction ease, etc. The external size of the bearing insert 20 may be varied to correspond to the internal dimensions of various sized trial head devices 30 but it is preferred to use a uniformly sized bearing insert to obviate repeatedly removing and replacing bearing insert 20 thereby reducing the time needed for the trial fitting process.

The outer trial head 30 is also preferably made of "Celcon" or "Delrin". Again, the material of choice is of little concern since the trial head will not be implanted.

Trial heads 30 are fashioned in a variety of spherical diameters, representative sizes having been discussed previously. For ease in selection and hence speed of procedure, the trial heads 30 can be made in various colors or otherwise coded or marked to facilitate side identification. Since it is preferred to use a uniformly sized bearing insert 20, the internal configurations of the trial heads 30 should be identically sized, with the possible exception of the chamfered lead-in surface 31 which facilitates quick and easy insertion of the bearing insert 20. The rearward opening 32, for accomodation of the rear portion 22 of the bearing insert 20, is shown as reduced in diameter from that of the main cavity 33 and is provided with a chamfered section 34 therebetween. Alternatively, cavity 33 and opening 32 could be unitary and of constant diameter throughout, i.e., cylindrical, in which event bearing insert 20 would similarly be of constant diameter throughout. An annular groove 35 is provided adjacent the lead-in surface 31 of trial head 30 to accomodate annular ring segment 25 of bearing insert 20.

FIG. 2 shows the various components assembled for trial insertion. The bearing insert 20 is first snapped onto the femoral ball 14, the resilient nature of the insert arms 21 allowing them to expand sufficiently to pass over and then grasp femoral ball 14.

This subassembly is then inserted into the cavity 33 of the trial head 30, the ends of the insert arms 21 deflecting inwardly until the annular ring segments 25 snap outwardly into place in the annular groove 35 of the trial head 30. The entire assembly is then rigidly locked together. Attempts to pull the assembly apart are futile because pulling on the femoral stem 11 causes ball 14 to force the insert arms 21 outwardly thus applying increased force on the annular ring segments 25 into and against the annular groove 35.

However, the assembly can be quickly and easily disassembled simply by pushing on the rearward protrusion 22 of the bearing insert 20 where it is exposed at opening 32 of the trial head 30. This action causes the annular ring segments 25 to be wedged inwardly and also the insert arms 21, whose inner curvature extends past the spherical surface of the femoral ball 14, to be deflected inwardly toward the neck portion 13 of the femoral prosthesis 10, thereby allowing the bearing insert 20 to be easily pushed out of the trial head 30.

While the preceeding description of the invention has been based on the use of the trial head and bearing insert with a femoral prosthesis stem, such usage would probably not be the common practice. The ball of an implantable femoral prosthesis has a very highly polished outer surface which might be accidentally scratched or marred during trial fitting procedures which can render the expensive prosthesis unusable. To preclude such possibility of damage, a trial handle would normally be used in conjunction with the trial head and bearing insert of the present invention for trial head size determination. The trial handle could terminate in a ball, similar in size and shape to that of the femoral prosthesis or it could be of an alternate design as will now be described.

Referring to FIG. 3, a handle 41 has fastened to one end thereof a button 43 and a bearing insert 44, held together by means of a stainless steel bolt 46. Button 43, typically formed of stainless steel stock although other materials such as acetal resins may be used, has a central bore axially therethrough and is provided at one end with a threaded shank to accommodate a locking collar 42 and a truncated spherical surface at its other end which fits into a spherical cavity in bearing insert 44. The assembly of button 43 and bearing insert 44 on handle 41 can then be snapped into trial head 40 and locking collar 42 threaded onto the shank of button 43 to lock the assembly into the trial head.

The bearing insert 44 is generally similar to the bearing insert 20 shown in FIGS. 1 and 2 except that it need not have the rearward protrusion 22 but instead has an opening 45 at its rear end to accommodate bolt 46, which fastens it and the button 43 to the handle 41.

The button 43 which is used instead of the femoral prosthesis ball 14 of FIGS. 1 and 2 is shown with a truncated spherical surface which is less than hemispherical as contrasted to the greater than hemispherical femoral prosthesis ball 14. It will, of course, be appreciated that the spherical surface of button 43 need not be truncated but can be truly spherical, the truncation merely being a matter of convenience in the manufacturing process of button 43. Since the top surface of button 43 is less than hemispherical and since it is securely fastened to the bearing insert 44 by bolt 46, there is no force tending to lock the bearing insert 44 into the trial head 40 when the assembly is pulled free of the trial head, i.e., when locking collar 42 is loosened, the trial handle 41, button 43 and bearing insert 44 can be easily and quickly snapped into and out of the trial head 40. When the assembly is snapped into place into the trial head 40, the locking collar 42 can be threaded against the bearing insert 44 which by camming action forces the annular ring segment 47 of the bearing insert 44 tightly into the groove 48 of the trial head making it impossible to remove the trial head 40 from the handle 41.

After the trial head 40 is tried for fit within the acetabulum, it may be pulled free, using the handle 41. The locking collar 42 can be unscrewed, the trial head 40 quickly and easily snapped off and replaced with another size of trial head 40, the locking collar 42 tightened again, and the process repeated.

What is claimed is:

1. A trial fitting device for an implantable femoral prosthesis comprising a trial head, a bearing insert removably fitting within said trial head and a femoral prosthesis stem or a trial handle having a ball on one end thereof onto which said bearing insert is removably rotatably mounted, said trial head comprising a substantially spherical body having a flat surface portion formed by removing a segment of a sphere therefrom thereby simulating the natural human femoral head and having a central bore extending axially through the flat surface portion, said bore having an annular groove formed therein adjacent the flat surface portion of said body, said bearing insert comprising a substantially cylindrical body having a plurality of flexible arms depending from one end thereof and a rigid cylindrical protrusion forming the other end, said flexible arms each having an annular ring segment on the exterior surface thereof adjacent its free end for locking action with the annular groove of said bore, said cylindrical body and the inner surfaces of said flexible arms being formed into a spherical cavity into which the ball of the femoral prosthesis stem is mounted, said spherical cavity comprising a larger segment of a sphere than the ball of said femoral prosthesis stem such that the free ends of said flexible arms extend past the spherical surface of said ball of said femoral prosthesis stem such that the free ends of said flexible arms can deflect inwardly to release the annular ring segments from the annular groove when pressure is applied on the rigid cylindrical protrusion of the bearing insert to thereby allow the bearing insert and attached femoral prosthesis stem to be removed from the trial head for replacement with a differently sized trial head.

2. A trial fitting device for an implantable femoral prosthesis according to claim 1 wherein said trial head is formed of a low-friction synthetic organic high temperature stable material capable of withstanding repeated steam sterilization cycles.

3. A trial fitting device for an implantable femoral prosthesis according to claim 2 wherein said bearing insert comprises a cylindrical body having a plurality of flexible depending arms formed by excising material from said cylindrical body between said arms and wherein said rigid cylindrical protrusion is of a reduced diameter from that of said cylindrical body.

4. A trial fitting device for an implantable femoral prosthesis according to claim 3 wherein said bearing insert is formed of a low-friction synthetic organic high temperature stable material capable of withstanding repeated steam sterilization cycles.

5. A trial fitting device for an implantable femoral prosthesis according to claim 4 wherein said femoral prosthesis stem has a greater than hemispherical ball on one end thereof onto which said bearing insert is removably rotatably mounted and wherein the spherical cavity in said bearing insert into which said greater than hemispherical ball is mounted comprises a larger segment of a sphere than said ball.

6. A trial fitting device for an implantable femoral prosthesis according to claim 4 wherein said trial handle has a greater than hemispherical ball on one end thereof onto which said bearing insert is removably rotatably mounted and wherein the spherical cavity in said bearing insert into which said greater than hemispherical ball is mounted comprises a larger segment of a sphere than said ball.

7. A trial fitting device for an implantable femoral prosthesis comprising a trial head, a bearing insert removably fitting within said trial head, a trial handle and a button with a spherical surface fitting within said bearing insert, said button and said bearing insert being removably affixed to said trial handle by suitable fastening means, said trial handle having a locking collar movably carried thereon for locking said button and bearing insert onto said trial head, said trial head comprising a substantially spherical body having a flat surface portion formed by removing a segment of a sphere therefrom thereby simulating the natural human femoral head and having a central bore extending axially through the flat surface portion, said bore having an annular groove formed therein adjacent the flat surface portion of said body, said bearing insert comprising a substantially cylindrical body having a plurality of flexible arms depending therefrom and a central bore extending through said cylindrical body, said flexible arms each having an annular ring segment on the exterior surface thereof adjacent its free end for wedging action with the annular groove of said bore, said button having a central bore axially therethrough, a threaded shank at one end and a less than hemispherical surface at its other end, said cylindrical body and the inner surfaces of said flexible arms being formed into a spherical cavity into which the hemispherical surface of the button is fitted, said spherical cavity permitting the free ends of said flexible arms to deflect inwardly to release the annular ring segments from the annular groove when said locking collar on said trial handle is loosened to thereby allow the trial handle and bearing insert and button to be removed from the trial head for replacement with a differently sized trial head.

* * * * *